United States Patent [19]

Peterson

[11] Patent Number: 4,838,864
[45] Date of Patent: Jun. 13, 1989

[54] PRESSURE CONTROLLER

[75] Inventor: Carl W. Peterson, Blackstone, Mass.

[73] Assignee: Mansfield Scientific, Inc., Mansfield, Mass.

[21] Appl. No.: 120,620

[22] Filed: Nov. 13, 1987

[51] Int. Cl.⁴ ............................................. A61M 29/00
[52] U.S. Cl. ..................................... 604/100; 604/118
[58] Field of Search ..................... 604/98, 99, 100, 118

[56] References Cited

U.S. PATENT DOCUMENTS

| | | |
|---|---|---|
| 4,064,879 | 12/1977 | Leibinsohn . |
| 4,403,988 | 9/1983 | Binard et al. . |
| 4,481,008 | 11/1984 | Kurtz . |
| 4,492,317 | 1/1985 | Guess et al. . |
| 4,612,010 | 9/1986 | Hamacher et al. . |
| 4,632,669 | 12/1986 | Phipps, Sr. et al. . |
| 4,723,938 | 2/1988 | Goodin et al. ................... 604/100 X |

FOREIGN PATENT DOCUMENTS

WO87/01945  4/1987  World Int. Prop. O. .

Primary Examiner—Allen M. Ostrager

[57] ABSTRACT

A pressure controller device for selectively applying and relieving a measured pressure upon a closed volume of fluid includes a housing, a barrel defining a fluid chamber and a plunger for axial movement within the fluid chamber for applying measured pressure to a fluid therewithin. The barrel has a port for delivery of fluid at measured pressure, and moves axially within the housing in a first axial direction in response to increased pressure within the chamber. The housing and barrel are biased apart, e.g., by a first biasing spring acting with a known force upon the barrel in an opposed, second axial direction. Indicia upon the barrel and housing indicate the relative positions of barrel and housing. As pressure in the fluid chamber increases, the barrel is urged in a first direction with a force proportional to the measured pressure to overcome the known force in the second direction, the relative positions of barrel and housing providing a measure of the pressure within the fluid chamber. An inflating and deflating assembly for balloon dilation, consisting, in combination, of the pressure controller device and a balloon catheter, is also described.

10 Claims, 7 Drawing Sheets

PRESSURE CONTROLLER

The invention relates to a pressure controller device, especially for inflation and deflation of a medical balloon catheter.

Devices for applying pressure to a liquid in a closed volume, e.g., a syringe connected to a balloon catheter, for inflation and deflation of the balloon within a patient's body have been described for use in dilatation and other medical procedures, e.g., in Fishione U.S. Pat. No. 4,655,749, Lundquist U.S. Pat. No. 4,439,185 and EP Publication No. 0.217,559. Such devices usually include gauges for indicating pressure within the syringe, typically a Bourdon tube or similar device connected to the device via a dead ended tube. Pressure controller devices having pressure gauges connected in this manner have the disadvantage of loss of pressure over time due to the gas/liquid interface between the inflation/deflation liquid and entrapped air, particularly in the connection tube to the gauge. The entrapped air is absorbed into the pressurized liquid, and the pressure drops as the liquid occupies the additional available volume left by absorbed air.

SUMMARY OF THE INVENTION

According to the invention, a pressure controller device for selectively applying and relieving a measured pressure upon a closed volume of fluid comprises a housing, a barrel defining a fluid chamber, and a plunger sized and constructed for axial movement within the fluid chamber for applying measured pressure to a fluid within the chamber. The barrel defines a port for delivery of fluid at the measured pressure, and is adapted for movement axially within the housing in a first axial direction in response to increased measured pressure within the chamber. The device also comprises first biasing means disposed between the housing and the barrel adapted to apply a known force upon the barrel in an opposed, second axial direction. Indicia means upon the barrel and upon the housing indicate the relative positions of the barrel and housing. As pressure in the fluid chamber increases, the barrel is urged in a first direction with a force proportional to the measured pressure to overcome the known force in the second direction of the first biasing means, the relative positions of barrel and housing providing a measure of pressure within the fluid chamber.

Preferred embodiments of the pressure controller device of the invention include one or more of the following features. The device further comprises a second biasing means disposed between housing and barrel adapted to apply a known force upon the barrel in the first axial direction, in opposition to force applied by the first biasing means, and the indicia means adapted for indicating a measured condition of negative pressure within the fluid chamber. The first and second biasing means are springs. The pressure controller device further comprises corresponding male and female threaded elements associated with the plunger for incremental threaded movement of the plunger axially within the barrel. Preferably the device comprises means for selective disengagement of male and female threaded elements for application of direct axial force upon the plunger; more preferably releasable means hold the threaded elements in disengagement during axial movement of the plunger. The plunger further comprises a tip element sized and constructed to engage the inner wall surface of the barrel in sealed, sweeping action. During use, the fluid chamber is filled with a liquid, and the device defines no regions of entrapped air in contact with the liquid. The port is sized and adapted for connection to a balloon catheter, whereby axial movement of the plunger in the barrel inflates the balloon to a measured pressure indicated by the relative positions of the indicia means on the barrel and housing.

According to another aspect of the invention, an inflating and deflating assembly for balloon dilation, comprising, in combination, the pressure controller device described above and a balloon catheter, is also described.

These and other features and advantages will be apparent from the following description of a presently preferred embodiment, and from the claims.

PREFERRED EMBODIMENT

We first briefly describe the drawings.

Drawings

FIG. 4 is a plan view of the threaded plunger of the pressure controller device, while FIG. 4A is an end view taken at line 4A—4A of FIG. 4, FIG. 4B is a plan view partially in section, of the plunger handle, FIG. 4C is a cross-sectional view of the handle taken at line 4C—4C of FIGS. 4 and 4B, and FIG. 4D is an enlargement of the buttressed threads of the plunger taken at line 4D—4D, while FIG. 4E is a similar view of alternate acme threads;

Figure 1:
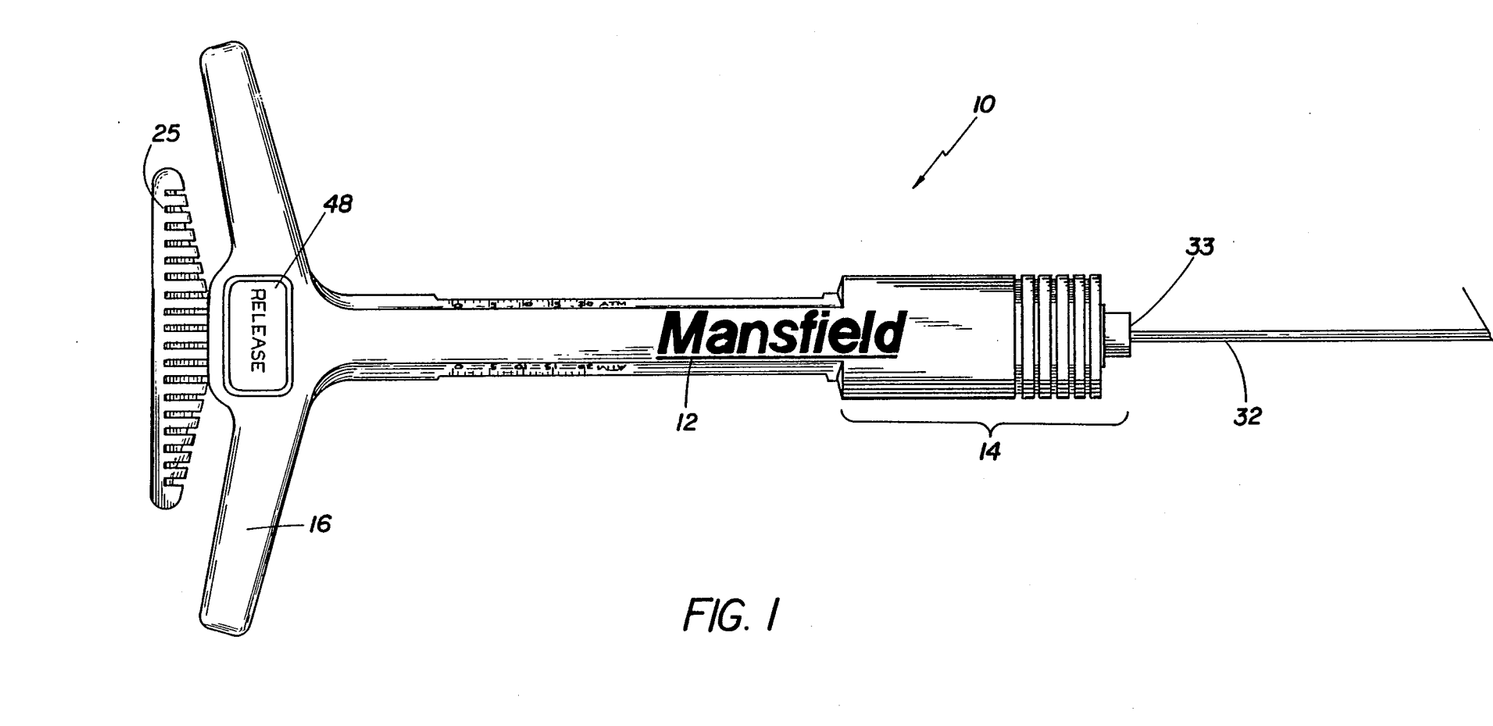
FIG. 1 is a plan view of the pressure controller device of the invention.
Figure 2:
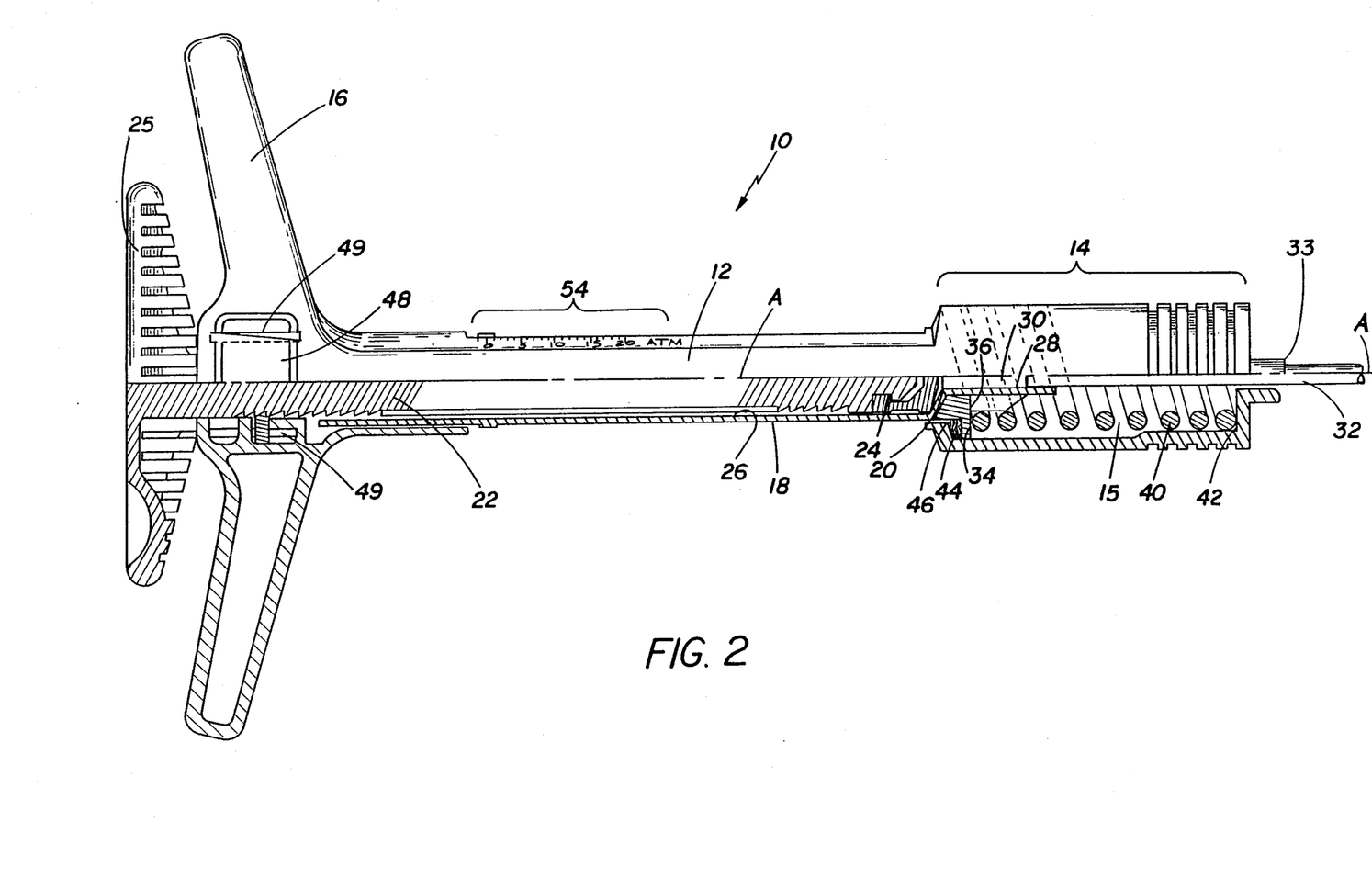
FIG. 2 is a plan view, partially in section, of the pressure controller device of FIG. 1.

Referring to FIGS. 1 and 2, the pressure controller device 10 of the invention consists of an elongated housing 12 having a distal portion 14 defining a cylindrical chamber 15 and a T-shape proximal handle 16.

Figure 3:
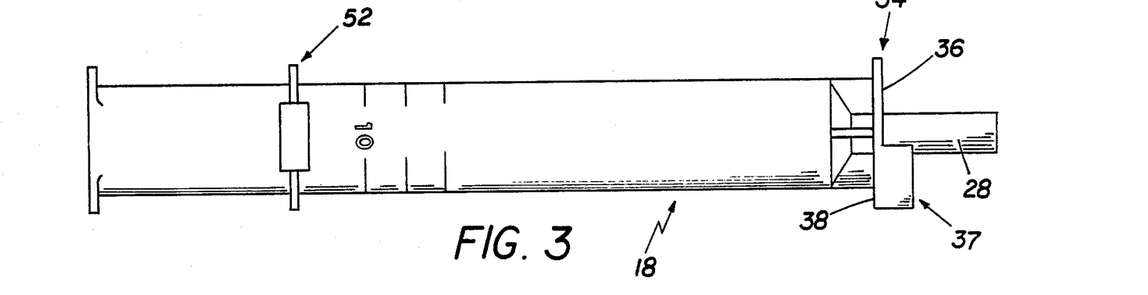
FIGS. 3 and 3A are plan and sectional views respectively of the syringe barrel.
Figure 3A:
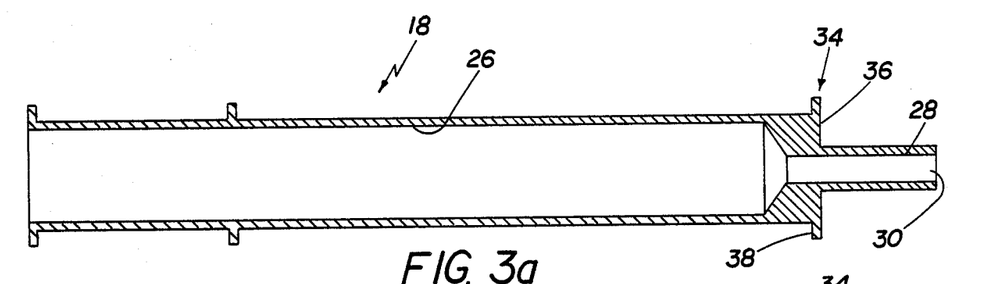
Figures 4, 4A, 4B, 4C, 4D, 4E:
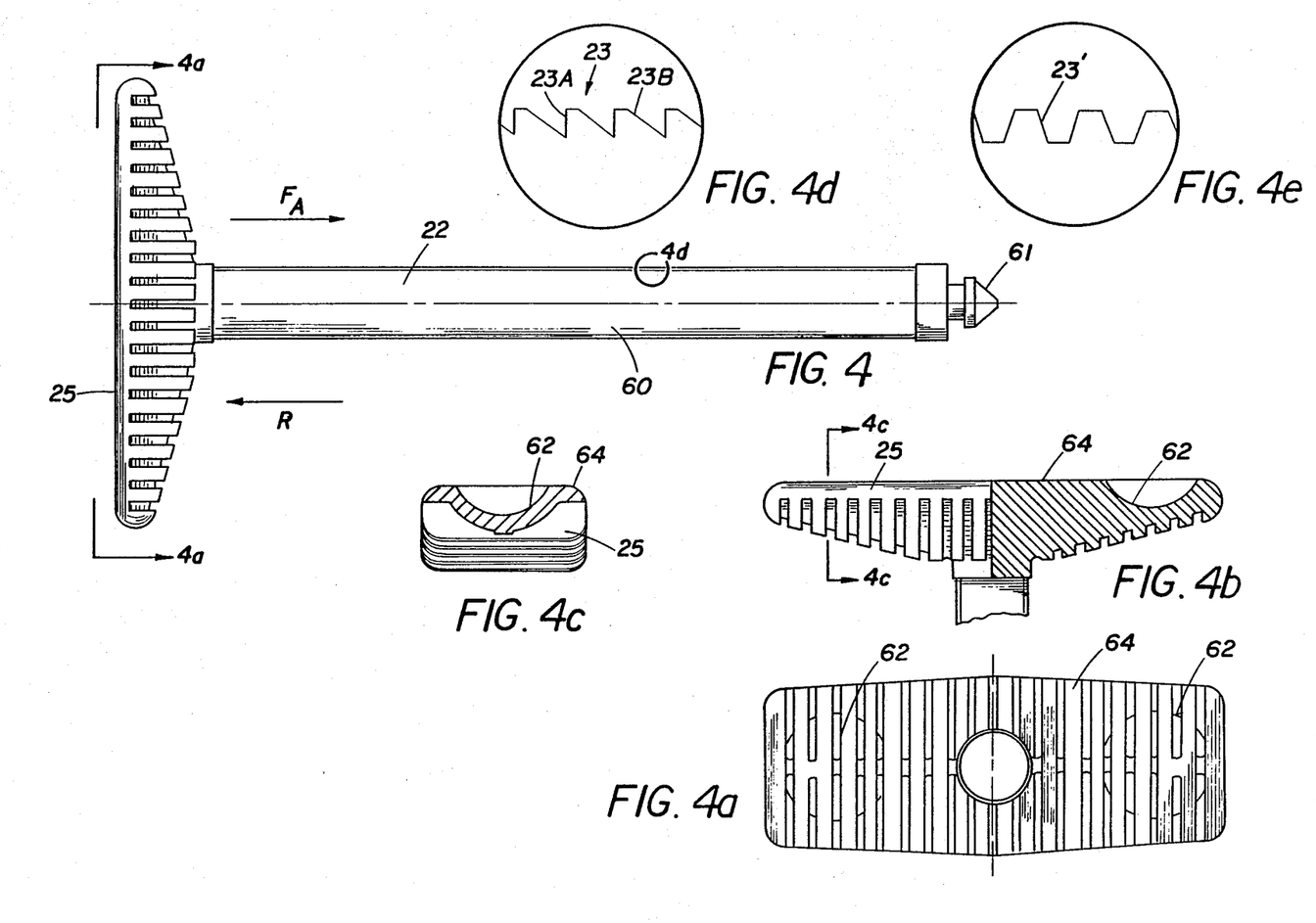

A syringe barrel 18 (FIGS. 3 and 3A), defining a fluid chamber 20, is mounted within the housing for axial movement proportional to pressure within the fluid chamber. A threaded plunger 22 (FIG. 4 et seq.) extends axially through the housing handle, into the syringe barrel, and terminates in a distal tip element 24, e.g., of rubber, that sweeps the wall surface 26 of the syringe barrel in sealing engagement. The plunger terminates proximally in a handle 25, as described more fully below.

The syringe barrel terminates distally in an elongated tip 28 defining a port 30. A flexible tubing 32, e.g., polyurethane, polyvinylchloride (PVC), nylon or other suitable material, is joined to the tip 28, e.g., by cementing or mechanical attachment, within the cylindrical chamber 15 and extends from the distal end 33 of the housing 12. The syringe barrel has an annular flange 34 disposed within chamber 15 to move along axis, A, as the syringe barrel moves, the flange defining a distally-directed surface 36 and a shoulder surface 38 directed in the proximal direction. Also disposed within chamber 15 about the distal tip of the syringe barrel and the tubular extension is a first biasing means (coil spring 40, FIGS. 5 and 5A) which engages the distal end surface 42 of chamber 15 and bears against the surface 36 of the syringe barrel flange with a known force. A second biasing means (wave spring 44, FIGS. 6 and 6A) is disposed within chamber 15 about the syringe barrel between the proximal end surface 46 of the chamber and the shoulder surface 38.

Figure 5:
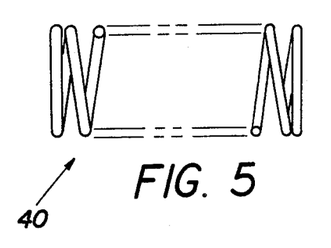
FIGS. 5 and 5A are side and end views of the first biasing means (coil spring)
Figure 5A:
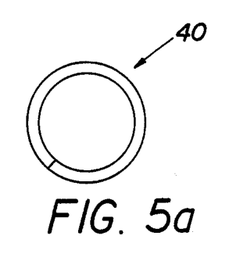
Figure 6:
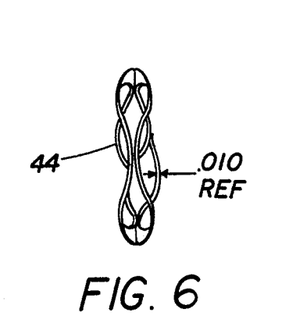
FIGS. 6 and 6A are side and end views of the second biasing means (wave springs)
Figure 6A:
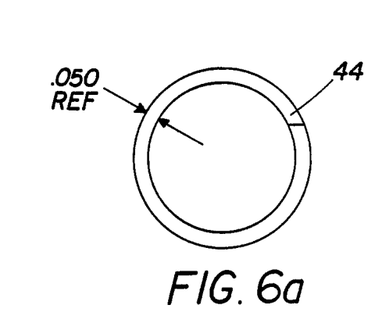

The coil spring 40 is a steel spring, e.g., of the type manufactured by Bay State Spring Corp. of Holden, Mass. The wave spring 44, is of stainless steel, having two turns crest to crest, 3.5 waves, edgewound and has a working height of 0.050 inch at 10 lbs., e.g., as manufactured by Smalley Steel Ring Company of Illinois.

Figure 7:
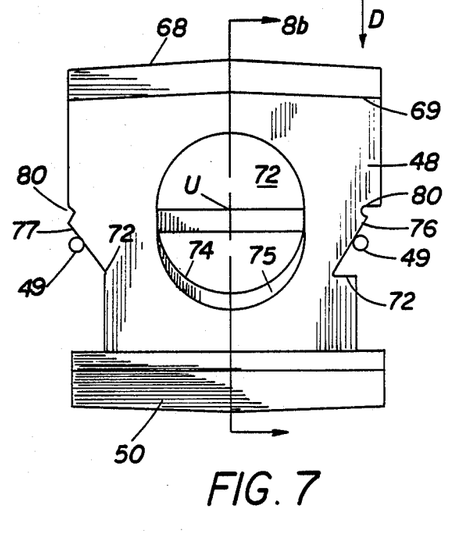
FIG. 7 is a side view of the RELEASE and LOCK elements in assembled condition with the spring wires.

Referring also to FIG. 7, the proximal end of the housing 12 contains a RELEASE element 48 (and associated wire springs 49 and four coil springs 53 (FIG. 10)) constructed for selectively engaging the threads of the plunger, e.g., buttress threads 23 (FIG. 4D) or acme threads 23' (FIG. 4E), for incremental threaded advancement or retraction of the plunger within barrel, for ratcheted advancement of the plunger into the barrel, and for disengagement from the threads of the plunger for direct axial movement of the plunger in the barrel. A LOCK element 50 is assembled with the RELEASE element and allows it to be retained in position, disengaged from the threads of the plunger. The RELEASE and LOCK elements are described more fully below.

Indicia 52, 54 on the syringe barrel and housing, respectively, indicate the position of the syringe barrel within the housing as a measure of pressure within the fluid chamber, as explained more fully below.

Syringe barrel 18 (FIGS. 3 and 3A), in the preferred embodiment, defines a 10 cc volume, although other size syringes may be employed. Typically the barrel is injection molded, e.g. from polycarbonate or rubber modified acrylic.

Plunger 22 (FIGS. 4 et seq.) is typically injection molded from glass reinforced polycarbonate and has an elongated shaft 60 with, e.g., buttress threads 23 (10 threads per inch, or other pitch as desired) along its length. The plunger terminates distally in conical tip 61 for fixedly receiving the rubber tip element 24 and terminates proximally in handle 25. The handle is sized for comfort of the user, with extended radial arms to provide leverage for cranking and adequate bulk for gripping and moving the plunger axially against the ratchet or with the threads completely disengaged, as described below. Depressions 62 are provided in the end surface 64 of the handle for engagement by the finger to allow use of the handle as a crank to rapidly wind the plunger in or out.

Referring now to FIG. 7 (and also to FIG. 10), RELEASE element 48 and LOCK element 50 (both formed, e.g., of reinforced nylon or polycarbonate, by injection molding) extend through the housing from opposite surfaces and are assembled by engagement of ridges 70 in slot 72 of element 50 within corresponding grooves 73 at the base of the side surfaces of element 48. The RELEASE element top surface 68 (FIG. 8) and the LOCK element top surface 51 (FIG. 9) are exposed at the surfaces of the housing. The RELEASE element defines an orifice 73 through which extends the buttress-threaded shaft of the plunger. The lower arc 74 of the orifice defines one or more partial threads 75, e.g., two are shown. In a first operating condition, the axis of plunger shaft 60 intersects lower center point T of orifice 72. Threads 75 of the RELEASE element are in threaded engagement with the threads 23 of the plunger and the plunger is advanced or retracted incrementally by rotation of handle 25. The RELEASE element is held in this first operating condition by coil springs 53 (FIG. 10) disposed between the housing and the under surface 69 of the RELEASE button, and by engagement of straight wire springs 49 upon ramp surfaces 76, 77 of element 48. The combination of the resilient wire and coil springs 49, 53 and the buttress thread construction of plunger 22, i.e., rear surfaces 23A at 90° to the shaft axis and front surfaces 23B at a lesser ramp angle (FIG. 4D), allows the plunger to be quickly moved forward, e.g., to achieve an initial pressure condition in fluid chamber 20, by application of axial force (in the direction of arrow $F_A$) upon the handle. The opposed angle surfaces of the partial threads 75 and the plunger threads 23 slide upon each other, causing the element 48 to move downward (arrow D) against the resilient force of wire springs 49 and coil springs 53. Ratcheting movement is prevented in the reverse direction (arrow R) by engagement of the opposed generally vertical surfaces 23A of the plunger threads and the retrograde surfaces 78 of partial threads 75.

Figure 8:
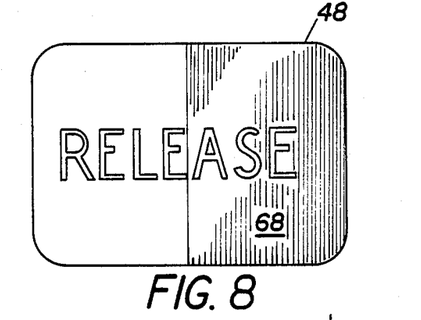
FIGS. 8, 8A and 8B are top, bottom and side section views respectively of the RELEASE element.
Figure 8A:
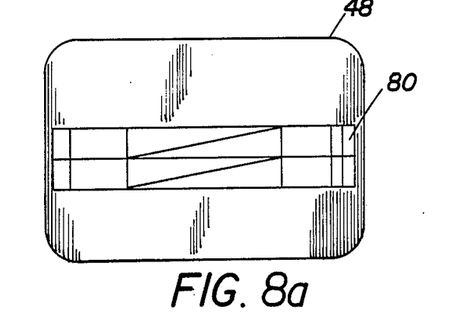
Figure 8B:
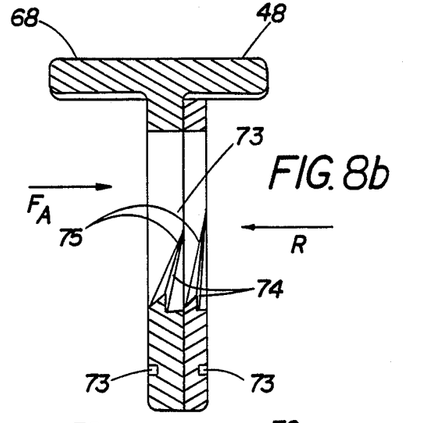
Figure 9:
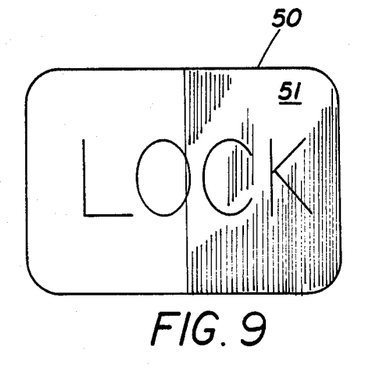
FIGS. 9, 9A and 9B are similar views of the LOCK elements.
Figure 9A:
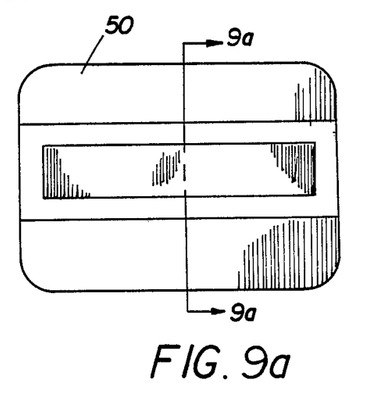
Figure 9B:
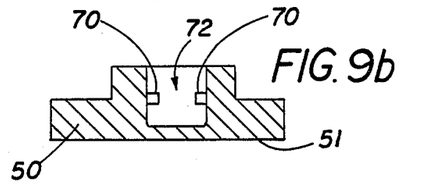

Movement of the plunger shaft in either forward ($F_A$) or reverse (R) direction is facilitated by applying pressure to RELEASE surface 68 to depress the assembled LOCK and RELEASE elements until the axis of the plunger shaft is moved toward intersection with center point U of orifice 73, and the plunger threads 23 are clear of partial threads 75. Application of additional force moves the assembly further downward, while causing the ramp surfaces 76, 77 to deflect the wire springs 49 outwardly until the springs engage in depressions 80 to hold the assembly with the threads disengaged. The wire springs may be freed of depressions 80, and the assembly returned to threaded engagement, by application of force to LOCK surface 51.

Figure 10:
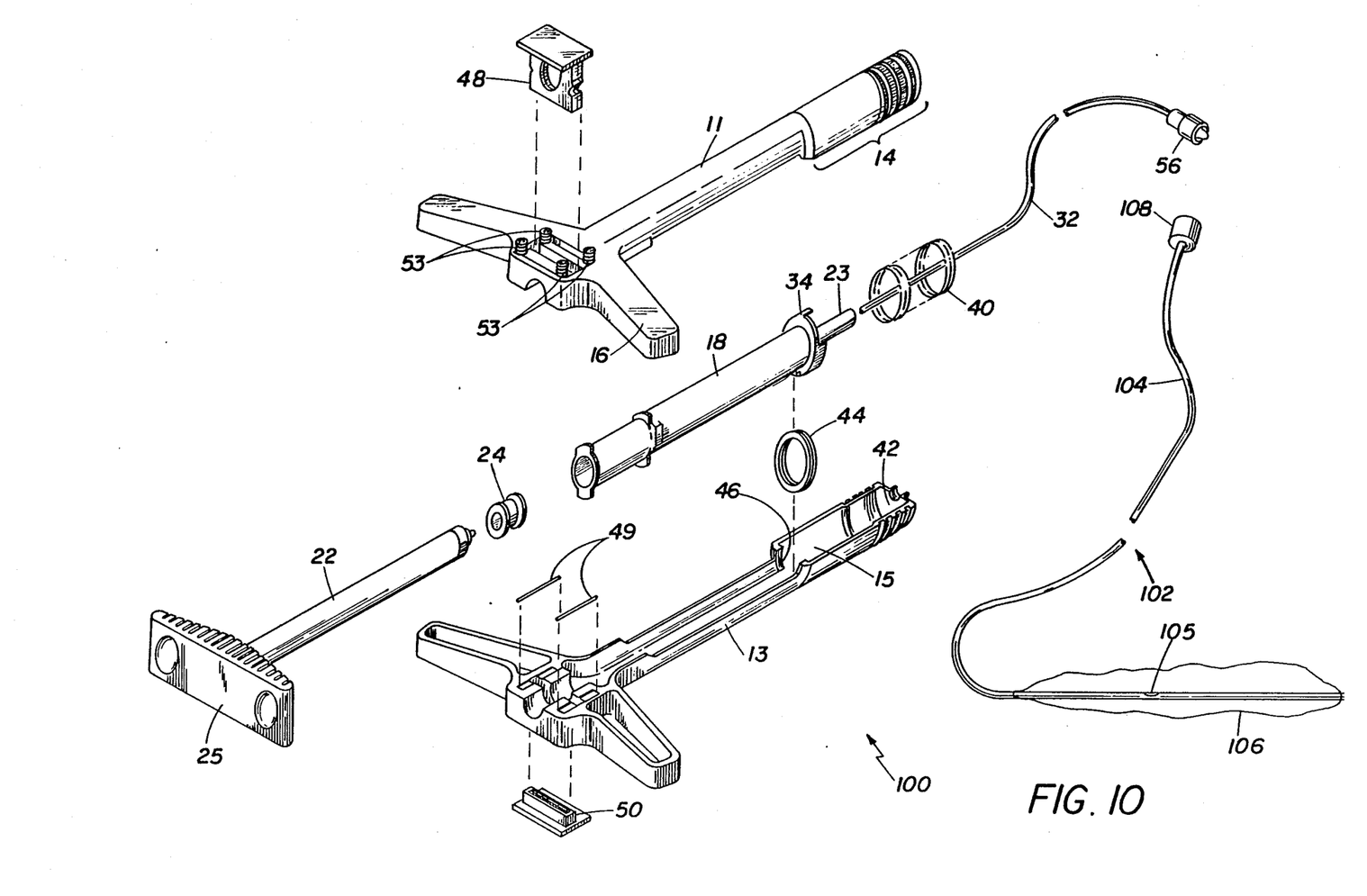
FIG. 10 is an exploded view of the inflating and deflating assembly of the invention, including the pressure controller device of FIG. 1 and a balloon catheter.
Figure 11:
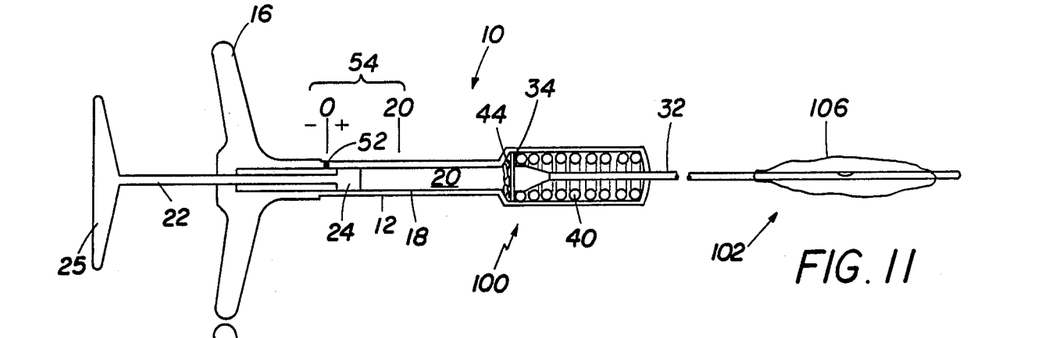
FIGS. 11 through 15 are somewhat diagrammatic representations of the inflating and deflating assembly of the invention in a sequence of balloon inflation and deflation.
Figure 12:
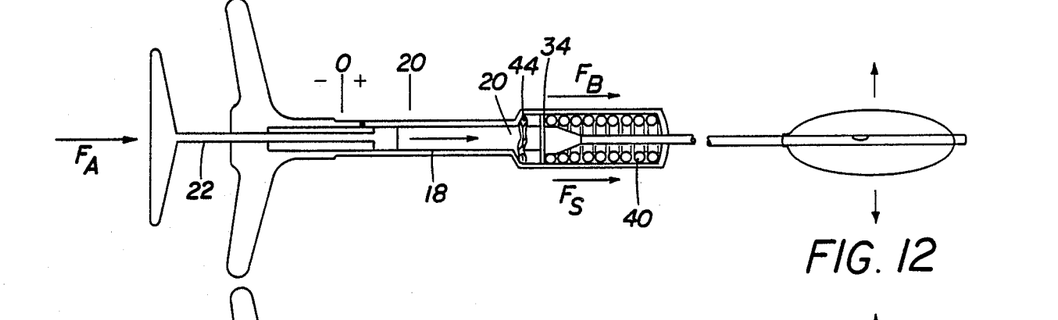
Figure 13:
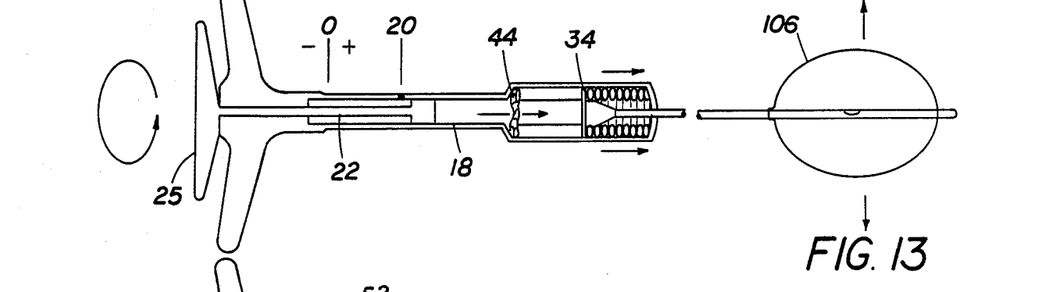

Referring now to FIG. 10, the elements of the pressure controller device 10 of the invention are shown in exploded view. The housing 12 consists of two mirror image components 11, 13 formed, e.g., of injection molded ABS, and joined, e.g., by ultrasonic welding. The tubular conduit 32 terminates distally in a male luer connector 56. The inflating and deflating assembly 100 of the invention consists of the pressure controller device 10 and, e.g., a balloon catheter 102 having an elongated catheter 104 defining a lumen that terminates (e.g., at port 105) within an inflatable balloon 106, typically adjacent the distal end. The catheter terminates proximally in a female luer connector 108 for attachment to male luer connector 56.

Referring now to FIGS. 11 through 15, and also to FIGS. 2 and 10, the pressure controller 10 is filled with an inflation fluid, e.g., contrast media, and purged of air. This is possible in the device of the invention because the distal tip element 24 of the plunger sweeps the volume of the barrel, and there are no dead-ended connecting tubes, e.g., as found in similar devices having Bourdon tube type pressure gauges. The balloon catheter 102 is also filled with liquid and purged of air.

The pressure controller device 10 is connected to the balloon catheter by joining male and female luer connectors 56, 108. The plunger 22 is withdrawn toward a rearward position to achieve a negative pressure within the balloon to ensure that it is fully deflated. At this point, spring coil 40 is extended, and the indicia 52 on the syringe barrel is at the "O Atmosphere" indicia 54 of the housing (FIG. 11) or to the negative side. The balloon 106 in this deflated state is advanced through the body of a patient to the site where dilatation is to occur, e.g., at a stenosis.

The plunger 22 is advanced (FIG. 12), typically first by application of axial force (arrow $F_A$) to ratchet the plunger forward to quickly achieve an intermediate pressure. As pressure is increased, the syringe barrel 18 is urged forward by the pressure applied upon the fluid within the fluid chamber 20. The force applied to the barrel in the forward direction $F_B$ compresses the spring coil 40, acting against the resistance of the known counteracting force of the spring coil ($F_s$) acting in the opposite direction. The barrel moves forward a distance proportional to the pressure of the fluid in the chamber, as indicated by the relative postions of the indicia 52, 54 on the barrel and housing. (The pressure in the chamber may be calculated from the known force constant of the spring, the surface area of the plunger tip (or piston) and the surface area of the syringe, and the syringe barrel and housing are calibrated for the distance of syringe barrel travel to indicate the pressure.)

Additional pressure may be applied (FIG. 13) by rotation of handle 25 to incrementally advance the plunger 22, the barrel 18 moving forward as well to reflect the increased pressure within the chamber, until the desired pressure in the chamber, and in the balloon 106 within the body, is achieved.

To deflate balloon 106, which it is typically medically desirable to do as quickly as possible, the plunger 22 is withdrawn (FIG. 14) by pressing the surface 68 of the RELEASE element 48 to disengage threads 23, 75 and allow the plunger to be moved by application of axial force (arrow $F_w$).

Figure 14:
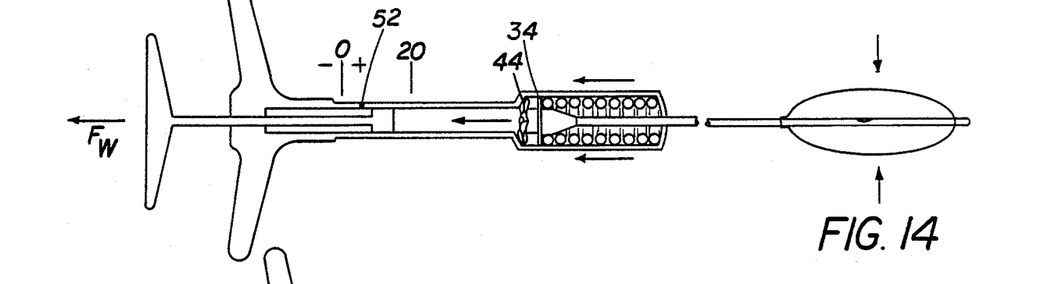
Figure 15:
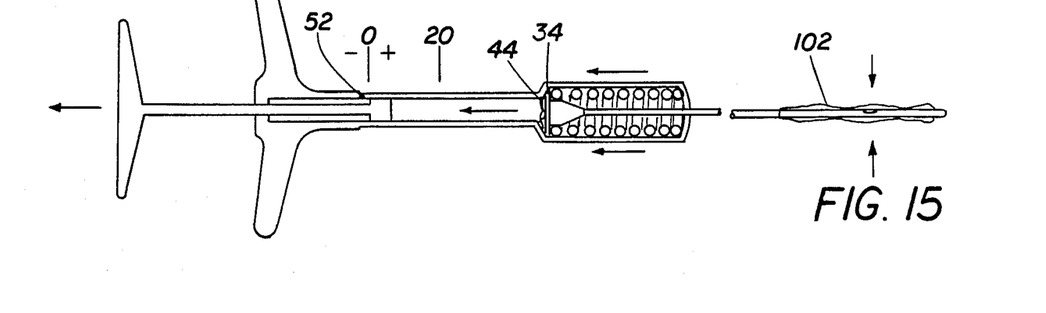

As pressure in the fluid chamber decreases, the barrel under force of coil spring 40 is moved rearwardly, and the decreasing pressure level is indicated by the relative positions of the barrel and housing indicia 52, 54.

The plunger is drawn rearwardly until a negative pressure is achieved (FIG. 15), ensuring that the balloon 106 is fully deflated. The negative pressure condition in the fluid chamber causes the barrel 18 to move rearwardly as well, against the known force of wave spring 44, and the barrel and housing indicia 52, 54 indicate a negative pressure condition.

Other embodiments are within the following claims. For example, the device and assembly of the invention may be disposable, intended for a single procedure. Syringe barrels of other volumes may be employed, e.g., depending upon the size of the balloon, and the pressure controller device may be constructed for operation at other pressure ranges, e.g., by changing the barrel or the springs. One or both of the biasing means may be hydraulic or pneumatic. The opposed threads may be arranged for positive engagement at increased pressure to reduce the possibility of accidental disengagement, e.g., the body of the release element may be disposed at an obtuse angle to the axis of the plunger.

Also, means may be provided to positively lock element 48 against disengagement of the threads above a predetermined fluid pressure in the chamber.

What is claimed is:

1. A pressure controller device for selectively applying and relieving a measured pressure upon a closed volume of fluid, comprising a housing,
    a barrel defining a fluid chamber,
    a plunger sized and constructed for axial movement within said fluid chamber for applying pressure to a fluid within said fluid chamber,
    said barrel defining a port for delivery of fluid at said pressure, and
    said barrel adapted for movement axially within said housing in a first axial direction in response to increase of said pressure within said chamber,
    first biasing means disposed between said housing and said barrel adapted to apply a known spring resistance in an opposed, second axial direction, to oppose said movement of said barrel, and
    indicia means upon said barrel and upon said housing for indicating the relative positions of said barrel and said housing,
    whereby, as pressure in said fluid chamber increases as a result of movement of said plunger relative to said housing, said barrel is urged in said first direction with a force proportional to said pressure to progressively overcome the known spring resistance in the second direction of said first biasing means, the relative positions of said barrel and said housing providing a measure of the pressure within said fluid chamber.

2. The pressure controller device of claim 1 further comprising a second biasing means disposed between said housing and said barrel adapted to apply a known spring resistance upon said barrel in the first axial direction, in opposition to spring resistance applied by said first biasing means, and
    said indicia means is adapted for indicating a condition of negative pressure within said fluid chamber.

3. The pressure controller device of claim 1 wherein said first and second biasing means are springs.

4. The pressure controller device of claim 1 or 2 further comprising corresponding male and female threaded elements associated with said plunger for incremental threaded movement of said plunger axially within said barrel.

5. The pressure controller device of claim 4 comprising means for selective disengagement of said male and female threaded elements for application of direct axial force upon said plunger.

6. The pressure controller device of claim 5 futher comprising releasable means for holding said threaded elements in disengagement during axial movement of said plunger.

7. The pressure controller device of claim 1 wherein said plunger further comprises a tip element sized and constructed to engage the inner wall surface of said barrel in sealed, sweeping action.

8. The pressure controller device of claim 1 wherein, during use, said fluid chamber is filled with a liquid, and said device defines no regions of entrapped air in contact with said liquid.

9. The pressure controller device of claim 1 wherein said port is sized and adapted for connection to a balloon catheter, whereby axial movement of said plunger in said barrel inflates the balloon to a pressure indicated by the relative positions of said indicia means on said barrel and said housing.

10. An inflating and deflating assembly for balloon dilation comprising, in combination, a balloon catheter, comprising an elongated conduit-defining catheter and a distal, inflatable balloon, and a pressure controller device for selectively applying and relieving pressure upon a closed volume of fluid, said pressure controller device comprising a housing, a barrel defining a fluid chamber, a plunger sized and constructed for axial movement within said fluid chamber for applying pressure to a fluid within said fluid chamber, said barrel defining a port sized and adapted for connection of said pressure controller device to said balloon catheter for delivery of fluid at said pressure through the conduit defined by said catheter for inflation and deflation of said balloon, and said barrel adapted for movement axially within said housing in a first axial direction in response to increase of said pressure within said chamber, first biasing means disposed between said housing and said barrel adapted to apply a known spring resistance in an opposed, second axial direction, to oppose said movement of said barrel, and indicia means upon said barrel and upon said housing for indicating the relative positions of said barrel and said housing, whereby, as pressure in said assembly increases as a result of movement of said plunger relative to said housing, said barrel is urged in said first direction with a force proportional to said pressure to overcome the known spring resistance in the second direction of said first biasing means, the relative positions of said barrel and said housing providing a measure of the pressure within said assembly.

* * * * *

UNITED STATES PATENT AND TRADEMARK OFFICE
CERTIFICATE OF CORRECTION

PATENT NO. : 4,838,864
DATED : June 13, 1989
INVENTOR(S) : Carl W. Peterson It is certified that error appears in the above-identified patent and that said Letters Patent is hereby corrected as shown below:

Abstract, line 20, "dilation" should read --dilatation--.

Column 3, line 22, "crest to crest" should read --crest-to-crest--.

Column 3, line 31, before "barrel" insert --the--.

Column 4, line 40, "Of" should read --of--.

Signed and Sealed this

Eighth Day of May, 1990

Attest:

HARRY F. MANBECK, JR.

Attesting Officer

Commissioner of Patents and Trademarks